United States Patent
Hutchenson et al.

(10) Patent No.: US 7,164,033 B2
(45) Date of Patent: *Jan. 16, 2007

(54) GAS PHASE SYNTHESIS OF METHYLENE LACTONES USING NOVEL CATALYST

(75) Inventors: Keith W. Hutchenson, Lincoln University, PA (US); Kostantinos Kourtakis, Media, PA (US); Leo Ernst Manzer, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/169,136

(22) Filed: Jun. 28, 2005

(65) Prior Publication Data

US 2006/0025612 A1    Feb. 2, 2006

Related U.S. Application Data

(60) Provisional application No. 60/591,518, filed on Jul. 27, 2004.

(51) Int. Cl.
- *C07D 307/02* (2006.01)
- *C07D 407/00* (2006.01)
- *C07D 305/12* (2006.01)
- *C07D 307/00* (2006.01)

(52) U.S. Cl. ...................... 549/295; 549/326

(58) Field of Classification Search ............ 549/295, 549/326

See application file for complete search history.

(56) References Cited

U.S. PATENT DOCUMENTS

| 6,313,318 | B1 | 11/2001 | Coulson et al. | |
|---|---|---|---|---|
| 6,723,790 | B1 | 4/2004 | Brandenburg et al. | |
| 2006/0025605 | A1* | 2/2006 | Hutchenson et al. | 549/263 |
| 2006/0025607 | A1* | 2/2006 | Hutchenson et al. | 549/263 |
| 2006/0025608 | A1* | 2/2006 | Hutchenson et al. | 549/263 |
| 2006/0025610 | A1* | 2/2006 | Hutchenson et al. | 549/263 |
| 2006/0025611 | A1* | 2/2006 | Hutchenson et al. | 549/263 |

FOREIGN PATENT DOCUMENTS

JP          10298172    * 11/1998

OTHER PUBLICATIONS

Machine translation of JP 10298172, paragraph 27-33, May 12, 2006.*
E. P. Barret, L. G. Joyner And P. P. Halenda, J. Amer. Chem. Soc., 73, 373 (1951).

* cited by examiner

*Primary Examiner*—Margaret D. Seaman
*Assistant Examiner*—Niloofar Rahmani
(74) *Attorney, Agent, or Firm*—Gerald E. Deitch

(57) ABSTRACT

Process for converting certain lactones to their alpha-methylene substituted forms that not only exhibits high initial activity (conversion), but also maintains a high level of activity with time on stream.

8 Claims, No Drawings

GAS PHASE SYNTHESIS OF METHYLENE LACTONES USING NOVEL CATALYST

CROSS-REFERENCE TO RELATED APPLICATION

This application claims priority under 35 U.S.C. §119 from U.S. Provisional Application Ser. No. 60/591,518, filed Jul. 27, 2004.

FIELD OF INVENTION

The invention pertains to a method of producing unsubstituted and substituted alpha-methylene lactones by a gas phase reaction of starting lactones with formaldehyde in the presence of a novel catalyst that not only exhibits high initial activity (conversion), but also maintains a high level of activity with time on stream.

BACKGROUND

Alpha-methylene-gamma-butyrolactone and methyl alpha-methylene-gamma-butyrolactone are useful monomers in the preparation of both homopolymers and copolymers. In addition, the alpha-methylene-gamma-butyrolactone group is an important structural feature of many sesquiterpenes of biological importance.

Current ways of making alpha-methylene-gamma-butyrolactone monomer are unattractive because of low yields, byproducts formation and/or expensive starting materials.

In particular, U.S. Pat. No. 6,313,318 describes a method for converting certain starting lactones to alpha-methylene substituted lactones using a so-called basic catalyst that is made by treating silica with an inorganic salt of Ba, Mg, K, Cd, Rb, Na, Li, Sr, and La. A problem inherent in the method is that there is a significant decrease in the conversion of the starting lactone to the alpha-methylene product with time on stream (TOS).

It would be advantageous, therefore, to have a lactone conversion process that not only exhibits high initial activity (conversion), but also maintains a high level of activity with time on stream.

SUMMARY OF THE INVENTION

This need is met by the present invention, which, in its first aspect, is a process for preparing a reaction product comprising an alpha-methylene lactone of the Formula II, said process comprising reacting a lactone of the Formula I with formaldehyde,

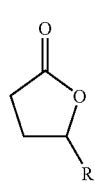

I

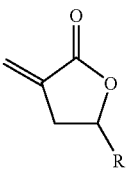

II wherein R is selected from the group consisting of hydrogen, methyl, ethyl, and straight or branched $C_3$–$C_5$ alkyl;

at a temperature in the range of from about 150° C. to about 450° C. in the presence of a catalyst;

said catalyst being made by (or obtainable by) a process comprising:

(a) contacting (i) porous silica, optionally containing at least one first element selected from the group consisting of aluminum, zirconium and titanium, said silica having a pore volume of at least 0.4 cc/g attributable to pores having a pore diameter between 65 and 3200 Angstroms, with (ii) a solution comprising a solvent and an organic compound of at least one second element selected from the group consisting of sodium, potassium, rubidium, cesium, and barium;

(b) drying the product of step (a) to remove at least a portion of said solvent;

(c) heating the product of step (b) to a temperature in the range of 350° C. to 550° C. to produce a catalyst precursor;

(d) flushing at a preselected flow rate an oxygen-containing gas over said catalyst precursor either during step (c), or after step (c) while the temperature is still in the range of 350° C. to 550° C. to produce a catalyst candidate comprising the at least one second element in an amount from about 0.1% to about 40% by weight of the combined weight of the catalyst candidate and the second element, or the combined weight of the catalyst candidate containing the at least one first element and the second element;

(e) determining by porosimetry whether said catalyst candidate has a pore volume of at least about 0.3 cubic centimeters per gram of catalyst attributable to pores having a diameter between 65 and 3200 Angstroms; and (f) if said catalyst candidate does not have a pore volume of at least about 0.3 cubic centimeters per gram of catalyst attributable to pores having a diameter between 65 and 3200 Angstroms, repeating, optionally more than once, steps (a) through (e) using in step (d) flow rates successively greater than said preselected flow rate until the catalyst candidate has a pore volume of at least about 0.3 cubic centimeters per gram of catalyst attributable to pores having a diameter between 65 and 3200 Angstroms.

In its second aspect, the present invention is the catalyst made by the process recited above.

The use of such a catalyst in the conversion of lactones of the Formula I to those of Formula II leads not only to high initial activity (conversion), but also to the maintenance of a high level of activity with time on stream.

DETAILED DESCRIPTION OF THE INVENTION

The following terms generally are abbreviated as follows:
"alpha-methylene-gamma-butyrolactone" is abbreviated MBL;
"gamma-butyrolactone" is abbreviated GBL;
"gamma-valerolactone" is abbreviated GVL;
"alpha-methylene-gamma-valerolactone" is abbreviated MVL;
"gamma-methyl alpha methylene gamma butyrolactone" is abbreviated MeMBL;
"time on stream" is sometimes abbreviated TOS;
"cubic centimeters" is abbreviated as cc or $cm^3$;
"mass spectroscopy" is abbreviated MS; and
"gas chromatography" is abbreviated GC.

The process of the present invention concerns a gas phase methylenation of lactones of Formula I to yield alpha-methylene lactones of Formula II.

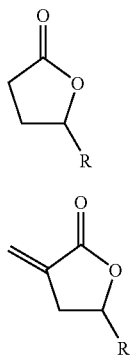

I

II

Specifically, lactone of Formula I is reacted with formaldehyde to give a reaction product comprising alpha methylene lactones of Formula II. The substituent —R group is selected from the group consisting of hydrogen, methyl, ethyl, and straight or branched $C_3$–$C_5$ alkyl. Also produced is an internal isomer of the lactone of Formula 11, represented by Formula III, below.

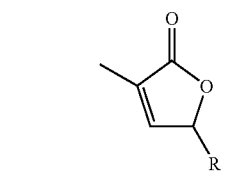

III

In a preferred embodiment the lactone of Formula I is gamma-butyrolactone (R is H) and the alpha-methylene lactone of Formula II is alpha-methylene-gamma-butyrolactone. In another preferred embodiment, the lactone of Formula I is methyl gamma-butyrolactone (R is methyl), and the alpha-methylene lactone of Formula II is gamma-methyl alpha-methylene gamma-butyrolactone.

The process of the present invention is carried out in the gas phase, at a temperature in the range of from about 150° C. to about 450° C. A temperature in the range of from about 250° C. to about 400° C. is preferred. A temperature in the range of from about 300° C. to about 340° C. is most preferred.

The reaction can be carried out at pressures ranging from about 0.1 MPa to about 1.0 MPa, with a preferred range of from about 0.1 MPa to about 0.5 MPa. Contact time with the catalyst can be selected to achieve desired yields and selectivities. Contact time can be manipulated by increasing or decreasing flow rates over the catalyst.

The formaldehyde may be supplied to the reaction in the form of an aqueous solution (formalin), a hemiacetal of an alcohol, a low molecular weight polyformaldehyde or formaldehyde trimer (trioxane). Formalin is preferred, because it is the lowest cost source of formaldehyde. The use of the trimers and oligomers, however, reduces the need to remove water from the process. Anhydrous formaldehyde can also be used. Hemiacetals work effectively, but require separate steps to release the formaldehyde from the alcohol and to recover and recycle the alcohol.

The catalyst used in the present invention comprises silicon and oxygen that form a matrix (or support) for a catalytic element. The catalytic element is at least one element selected from the group consisting of sodium, potassium, rubidium, cesium, and barium. Barium is preferred, because it minimizes the formation of the isomer of Formula II. The catalytic element is deposited on or dispersed within the matrix by contacting the matrix with a solution of an organic compound of at least one of these elements. The matrix comprising silicon and oxygen can optionally comprise at least one compound comprising an element selected from the group consisting of titanium, aluminum and zirconium. The catalytic element should constitute from about 0.1% to about 40% by weight of the combined weight of the catalyst and the added catalytic element (as opposed to the entire compound of which the element is a part).

The catalyst must be porous and have a pore-size distribution such that those pores having a diameter between 65 and 3200 Angstroms provide a pore volume of at least about 0.3 cubic centimeters per gram of the catalyst.

In some cases, reaction conditions may result in a decrease of catalyst efficiency. In these situations it may be useful to periodically reactivate the catalyst. For example, contacting the present catalysts, when activity drops below an acceptable level, with oxygen at elevated temperatures has the effect of reactivating the catalyst. Contact temperatures with oxygen may range from about 225° C. to about 500° C., with temperatures of about 250° C. to about 425° C. being preferred.

Selectivities and yields of product may be influenced by the total contact time with the catalyst. As stated previously, yields and selectivities may be increased by adjusting gas and liquid flow rates.

Separation and/or purification of the desired products, including MBL or MeMBL, from unreacted starting lactone and/or reaction byproducts may be performed by processes known in the art. A particularly suitable method to recover the desired product is to polymerize MBL in GBL solution, or MeMBL in GVL solution, using standard free-radical polymerization, isolate the polymer by precipitation, and then thermally depolymerize back to MBL or MeMBL, as the case may be, by heating under vacuum. Separation of the MeMBL from the internal isomer of Formula III can be accomplished by the polymerization of MeMBL. An appropriate polymerization technique is taught in U.S. Pat. No. 6,723,790. Finally, MBL can be separated from GBL by melt crystallization. Another effective method is liquid-liquid extraction.

Non-limiting reactors suitable for the process of the instant invention include a tubular reactor, fluidized bed reactor, fixed bed reactor, and transport bed reactor. The process can be run in either batch or continuous mode as described, for example, in H. Scott Fogler, *Elements of Chemical Reaction Engineering*, 2$^{nd}$ Edition, Prentice-Hall Inc, Calif., 1992.

The reaction can be carried out by passing solutions of the formaldehyde and lactone over the catalyst at elevated temperatures.

The catalysts of the present invention can be made by (or are obtainable by) a method as follows.

Porous silica powder, such as the material sold by Grace Davison, Inc. (Columbia, Md.) with a pore volume of at least 0.4 cc/g attributable to pores having a diameter between 65 and 3200 Angstroms is used as a catalyst matrix. Porosity preferably is determined by mercury porosimetry. Preferably the porous silica contains compounds of aluminum, titanium and/or zirconium. These latter silicas are preferred because of their hydrothermal stability.

A suitable way of choosing appropriate starting porous silica is to eliminate first those silicas that have a mean pore diameter less than 65 Angstroms and porosity less than 0.4 cc/g attributable to pores having diameters between 65 and 3200 Angstroms. Next, a porous silica manufacturer that describes its products in terms of mean pore diameter can be consulted to see if the manufacturer has the underlying data from which the mean pore diameter was calculated. If so, the manufacturer may be able to specify which, if any, of its products have pore volumes of greater than 0.4 Angstroms attributable to pores having diameters between 65 and 3200 Angstroms. These materials preferably should be independently tested by mercury porosimetry to determine that they meet the porosity characteristics required by this invention.

Organic compounds such as the carboxylates, such as acetate, propionate, butyrate, and 2-ethylhexanoate of a catalytic element selected from the group consisting of sodium, potassium, rubidium, cesium, and barium is dissolved in aqueous or non-aqueous solvent and contacted with the porous silica. Organic compounds do not include carbonates of the aforesaid catalytic elements. Organic compounds containing acetates are preferred. Other organic anions such as acetylacetonates can be used. One convenient method for introducing the catalytic element into the porous silica is to dissolve a suitable weight of the organic compound of the catalytic element in just enough solvent to equal the volume of the pores of the selected amount of the porous silica. The amount of organic compound should be chosen to provide to the silica from 0.1 wt % to 40 wt % of the element relative to the combined weight of the porous silica plus the element (as opposed to the compound of which the element is a part). This procedure should ensure that the proper amount of the element is present in the final catalyst. The resulting material is allowed to dry, preferably in a nitrogen environment for an extended time. The purpose of the drying is to remove at least a portion of the solvent in which the organic compound is dissolved.

Organic compounds such as the alkoxides can also be used. Organic alkoxides of an element selected from the group consisting of sodium, potassium, rubidium, cesium, and barium can contain from one to 20 carbon atoms and preferably 1 to 5 carbon atoms in the alkoxy group. The organic alkoxide should be soluble in the solvent. Most alkoxides can be dissolved in non-aqueous solutions such as ethanol, propanol, or isopropyl alcohol. Subsequent methods for introducing the element and drying are the same.

The dried material is then heated (for example in an alumina boat placed in a tube furnace) at an ambient temperature of 350° C. to 550° C. (The temperature of the catalyst material may be somewhat higher because of exothermic reactions taking place on the material.) A temperature between 450° C. and 550° C. is preferred. Either during the heating or subsequent to it, but at the same temperature, the material is flushed with an oxygen-containing gas (e.g. air), which is believed to burn off organic residues formed during the heating step. In a tube furnace, an airflow rate of at least 110 cc/min in a 3 cm diameter tube furnace, which corresponds to a linear velocity of 15.6 cm/min was found to be acceptable. Use of sufficiently high airflow rates is important to produce a high surface area material. In a tube furnace, the material can be heated at a rate of 5° C./min to 120° C., and can be exposed to this temperature for 4 hours. It can be heated subsequently at a rate of 5° C./min to approximately 450° C. and held at this temperature for 16 hours. Other equipment can be used to perform the heating step. Such equipment includes fluidized bed and rotary calcination equipment.

Heating can be accomplished in air or in a combination of an inert gas such as nitrogen, argon, or krypton for parts of the cycle, followed by air. An initial drying step at 120° C. in nitrogen, another inert gas, or air is preferred for a period of 30 minutes to 24 hours. Following this drying step, the catalyst can be heated in air or nitrogen to a temperature of 350° C. to 550° C. For acetate precursors, 450° C. to 550° C. is required. Heating times can range from 30 minutes to 48 hours. The final heating step preferably is performed in air for at least 30 minutes.

Once the catalyst is made as described above, it can be tested to confirm that it has a pore volume of at least about 0.3 cc/g of catalyst attributable to pores having a diameter between about 65 and 3200 Angstroms. (The reason that the porosity of the starting porous silica decreases after treatment is believed to be attributable to the inclusion of the catalytic element into the silica.)

Pore volume may be obtained by a variety of techniques, but preferred techniques are mercury (Hg) and nitrogen porosimetric techniques, with Hg porosimetry being most preferred.

Mercury porosimetry data can be obtained at 414 MPa using, for example, a Micromeritics 1 Model 9420 AutoPore III Instrument (Micromeritics Inc., One Micromeritics Drive, Norcross Ga. 30093-1877). This technique permits one to measure the pore volume and size by forcing mercury to penetrate inside the open porosity. Mercury is used because it behaves as a non-wetting liquid with a large number of materials.

Mercury is forced to enter into the pores by applying a controlled increasing pressure. As a sample holder is filled with mercury under vacuum conditions, mercury surrounds the sample without entering the pores due to the very low residual pressure. During the test, the pressure is increased, and the volume of mercury penetrated is detected by means of a capacitive system. The decreasing volume of mercury in the sample holder represents the pore volume. The penetration pressure is directly related to the pore access size by a well-known mathematical model, expressed by the Washburn equation:

$$D = -4 \gamma \cos(\theta)/Pc$$

Where:

$\gamma$ is surface tension of pure mercury (480 dyne/cm);

$\theta$ is contact angle between mercury and the solid (average value 140° C.);

Pc is mercury penetration equilibrated pressure; and

D is pore diameter.

The distribution of pore size, as well as the total porosity, bulk and apparent density and the specific pore volume can be obtained by the relationship between the pressure necessary for penetration (the pore dimension) and the volume of penetrated mercury (pore volume). At each pressure, therefore, a differential volume of Hg can be calculated which occupies the pores of the solid; this represents the additional Hg volume which is intruded as a consequence of a pressure increase. At lower applied pressure, larger pores are filled with Hg. With increasing applied pressure, smaller pores are occupied up to the smallest pore diameter reasonably measurable by this technique, 65 Angstroms. In this way, a distribution of pore sizes as a function of applied pressure can be obtained.

Pores are assumed to be of a cylindrical shape, as is standard for this technique.

Sample compressibility correction is calculated post priori by determining the volume of samples and pores not yet intruded as a function of applied pressure. The resulting relationship is used to correct the raw intrusion data for sample compression effects.

From the Washburn equation it is clear that the pore size range that can be investigated by mercury porosimetry is directly related to the pressure range.

Alternatively, nitrogen porosimetry may be used. Dinitrogen adsorption/desorption measurements can be performed at 77.3° K using, for example, Micromeritics ASAP model 2400/2405 porosimeters. Samples can be degassed at 150° C. overnight prior to data collection. Pore volume distributions can be determined using a 27 point desorption isotherm and can be analyzed using the BJH method.decribed in E. P. Barret, L. G. Joyner and P. P. Halenda, *J. Amer. Chem. Soc.*, 73, 373(1951).

In this invention, pores having diameters of 65 Angstroms up to 3200 Angstroms should contribute at least 0.3 cc/g pore volume to the final catalyst. Above 3200 Angstroms, inter-particle pores and void spaces are measured, and are not important for this invention.

If the catalyst possesses the correct porosity, it may be used in the lactone conversion method. If not, it may be necessary to repeat the catalyst synthesis using higher oxygen-containing gas flow rates than were used initially. The process may have to be repeated several times with successively higher gas flow rates until a catalyst with the correct porosity is finally obtained.

COMPARATIVE EXAMPLES

Comparative Example 1

Comparative Catalyst 1 ("CC1") (20% by Weight of Rb, on Davicat® Si 1251; Small Pore Volume Silica)

About 20 g of $SiO_2$ powder, Davicat® Si1251 (Grace Davison, Inc., Columbia, Md.) having a pore volume of 0.36 $cm^3/g$ was used as support material to make the catalyst support. 8.45 g of rubidium acetate (Aldrich Chemical Co.) was dissolved in enough water to match the pore volume of the Si 1251 support; that is, enough solution was added to approximately fill the pores of the support. The amount of water used was approximately 7.2 $cm^3$. The material was allowed to dry for at least 12 hours in a nitrogen environment. Approximately 10 $cm^3$ of the material was loaded into an alumina boat and heated in a tube furnace. The internal diameter of the tube furnace was 10 cm. The airflow rate was greater than 1220 $cm^3/min$, which corresponds to a linear velocity of greater than 15.6 cm/min. Use of this higher airflow is important to produce a high surface area material. The material was heated at a rate of 5° C./min to 120° C.; this temperature (120° C.) was maintained for four hours. It was subsequently heated at a rate of 5° C./min to approximately 450° C. (as measured by a thermocouple placed approximately 0.5 cm over the catalyst bed) and was held at this temperature for 16 hours.

The catalyst produced as described above has a porosity of less than 0.01 cc/g, and, therefore, does not have the porosity characteristics required by the present invention, i.e., greater than 0.3 cc/g attributable to pores having diameters between 65 and 3200 Angstroms.

Comparative Example 2

Comparative Catalyst 2 ("CC2")

An example described in U.S. Pat. No. 6,313,318B1 was duplicated. In a 100 ml round bottom flask, 25 ml of solution of 1.86 wt % Ba (as the hydroxide) in $H_2O$ were combined with 5.0 grams of silica (Grace Davison, grade 57, 10–20 mesh). The slurry was stirred at room temperature for 10 minutes. $H_2O$ was removed by rotovac evaporation. The solid was heated at 550° C. for two hours in flowing nitrogen.

EXAMPLES OF THE INVENTION

Catalyst 1(20% by Weight of Rb on Davicat® Si1700, $SiO_2$ Support)

The procedure outlined in Example 1 was used with a Davicat® Si1700 support (Grace Davison, Inc., Columbia Md.) instead of Si1251. Davicat® Si 1700 is an $SiO_2$ powder, and has a greater pore volume than Davicat® 1251 (approximately 1.57 cc/g). Therefore, 31.4 $cm^3$ of water was used, instead of 7.2 $cm^3$ as in Example 1.

Catalyst 2 (20% by Weight of Rb, on Davicat® Si 1405, $SiO_2$ Support)

The procedure outlined in Example 1 was used with a Davicat® Si1405 support (Grace Davison, Inc., Columbia Md.) instead of Davicat® Si 1251. Davicat® Si 1405 is a $SiO_2$ powder which has a greater pore volume than $SiO_2$ 1251 (approximately 1.10 cc/g). Therefore, 22.0 $cm^3$ of water was used, instead of 7.2 $cm^3$ as in Example 1. The same heating protocol was used as described in example 1, except that a 3 cm diameter tube furnace was used instead of a 10 cm diameter tube furnace. In this tube furnace, an airflow rate of at least 110 cc/min was used, which corresponds to a linear velocity of 15.6 cm/sec. The material was heated at a rate of 5° C./min to 120° C. The temperature was held at 120° C. for four hours. The material was subsequently heated at a rate of 5° C./min to approximately 450° C. (as measured by a thermocouple placed approximately 0.5 cm over the catalyst bed) and was held at this temperature for 16 hours and allowed to cool to room temperature in air.

Catalyst 3 (20% by Weight of Rb, on Davicat® Si 1415, $SiO_2$ Support)

The procedure outlined in Example 1 was used with an Davicat® Si 1415 support (Grace Davison, Inc., Columbia Md.) instead of Davicat® Si 1251. Davicat® Si 1415 has a greater pore volume than Davicat® Si 1251 (approximately 0.85 cc/g). Therefore, 17.0 $cm^3$ of water was used, instead of 7.2 $cm^3$ as in Example 1.

Catalyst 4 (20% by Weight of Rb, on Davicat® ZrSi4101, Zr—SiO$_2$ Support)

The same procedure as described in example 1 was used, except for the following differences: 20 g of Davicat® SiZr 4101 support was used, and 8.45 g of rubidium acetate was dissolved in 19.60 g of water and impregnated into the support.

Catalyst 5 (20% by Weight of Rb, on Davicat® SiTi 4151, Ti—SiO$_2$ Support)

The same procedure as described in example 1 was used, except for the following differences: 20 g of Davicat® SiTi 4151 support was used, and 8.45 g of rubidium acetate was dissolved in 20.0 g of water and impregnated into the support.

Catalyst 6 (20% by weight of Cs, on Davicat® Si 1700, SiO$_2$ Support)

The same procedure as described in example 1 was used, except for the following differences: 20 g of Davicat® Si1700 support was used. 7.22 g of cesium acetate was dissolved in 29.0 g of water and impregnated into the support.

Catalyst 7: (20 wt % Cs, on Davicat® Si 1405, SiO$_2$ support)

The same procedure as described in example 1 was used, except for the following differences: 20 g of Davicat® Si 1405 support was used. 7.22 g of cesium acetate was dissolved in 19.0 g of water and impregnated into the support.

Catalyst 8: (20 wt % Ba, on Davicat® SiTi 4551, Ti—SiO$_2$ support)

The same procedure as described in example 1 was used, except for the following differences: 20 g of Davicat® SiTi4551 support was used. 9.30 g of barium acetate was dissolved in 20 g of water and impregnated into the support.

Catalyst 9: (10.7 wt % K, on Davicat® Si 1415, SiO$_2$ support)

The same procedure as described in example 1 was used, with the following differences: 5.74 g of potassium acetate was dissolved in 17.0 g of water, which was impregnated into 20 g of Davicat® Si1415 powder, which was used as the support.

Catalyst 10: (6.3 wt % Na, on Davicat® Si 1700, SiO$_2$ support)

The same procedure as described in example 1 was used, with the following differences: 7.96 g of sodium acetate was dissolved in 31.40 g of water, which was impregnated into 20 g of Davicat® Si1700 powder, which was used as the support.

TABLE 1

Mercury Porosimetry Data of Catalysts

| Cat. No. | Composition wt % = (wt element/(wt Support + wt element) × 100 | Pore Volume (cc/g) from pores having diameter of 65 A or greater |
|---|---|---|
| CC1 | 20% Rb/Si 1251 | <0.01 |
| CC2 | Ba(OH)$_2$/SiO$_2$ | 0.926 |
| 1 | 20% Rb/Si 1700 | 1.04 |
| 2 | 20% Rb/Si 1405 | 0.908 |
| 3 | 20% Rb/Si 1415 | 0.723 |
| 4 | 20 wt % Rb/ZrSi4101 | 0.313 |
| 5 | 20 wt % Rb/SiTi 4151 | 0.732 |
| 6 | 20 wt % Cs/Si 1700 | 0.817 |
| 7 | 20 wt % Cs/Si 1405 | 0.889 |
| 8 | 20 wt % Ba on SiTi 4551 | 0.63 |
| 9 | 10.7 wt % K/Si 1415 | 0.838 |
| 10 | 6.3 wt % Na/Si 1700 | 0.871 |

Example of Gas Phase Reaction

Solutions containing gamma-valerolactone in formalin (37% aqueous formaldehyde), at various feed ratios, were fed to a vaporizer (held at 200° C.) followed by the introduction of nitrogen, to carry the vapor through a ¼ inch tubular reactor containing a catalyst heated to the appropriate reaction temperature. In the following examples, nitrogen flow rate was 24 cc/min., liquid feed rate was 1 ml/hr, formaldehyde to GVL molar ratio was 4:1, and the catalyst volume was 2 cc. The TOS (hours) was typically 4 to 6 hours. The reactor effluent was condensed in a cold trap and analyzed off-line by GC-MS using an internal standard. Conversion is based on the weight percent of GVL converted, and selectivity was based on the weight fraction of each compound relative to the amount of GVL converted.

TABLE 2

Reaction Data

| Cat. No. | Weight % catalytic Metal/Support | GVL Conversion | Selectivity to MeMBL Isomers | TOS (Hours) |
|---|---|---|---|---|
| CC1 | 20% Rb/Si 1251 | 1.29 | >90% | 0.5 |
|  |  | 1.10 | >90% | 2 |
|  |  | 1.01 | >90% | 5 |
| CC2 | Ba(OH)$_2$/SiO$_2$ | 28.8 | >90% | 0.5 |
|  |  | 15.96 | >90% | 2 |
|  |  | 9.42 | >90% | 5 |
| 1 | 20% Rb/Si 1700 | 36.21 | >90% | 0.5 |
|  |  | 62.09 | >90% | 2.0 |
|  |  | 52.32 | >90% | 5 |
| 2 | 20% Rb/Si 1405 | 67.55 | >90% | 0.5 |
|  |  | 57.2 | >90% | 2 |
|  |  | 52.0 | >90% | 5 |
| 3 | 20% Rb/Si 1415 | 28.43 | >90% | 0.5 |
|  |  | 26.21 | >90% | 2 |
|  |  | 28.28 | >90% | 5.5 |
| 4 | 20 wt % Rb/ZrSi4101 | 45.85 | >90% | 0.75 |
|  |  | 32.16 | >90% | 2 |
|  |  | 18.81 | >90% | 5.5 |
| 5 | 20 wt % Rb SiTi 4151 | 60.9 | >90% | 0.5 |
|  |  | 45.25 | >90% | 0.25 |
|  |  | 41.19 | >90% | 4 |
| 6 | 20 wt % Cs/Si 1700 | 48.2 | >90% | 0.5 |
|  |  | 42.82 | >90% | 3.0 |
|  |  | 45.39 | >90% | 5 |
| 7 | 20 wt % Cs Si 1405 | 56.25 | >90% | 0.5 |
|  |  | 46.90 | >90% | 2 |
|  |  | 45.64 | >90% | 5 |
| 8 | 20 wt % Ba/SiTi 4551 | 47.74 | >90% | 0.5 |
|  |  | 28.05 | >90% | 2.0 |
|  |  | 20.40 | >90% | 5 |
| 9 | 10.7 wt % K/Si 1415 | 34.48 | >90% | 0.5 |
|  |  | 36.51 | >90% | 2.0 |
|  |  | 42.61 | >90% | 5 |
| 10 | 6.3 wt % Na/Si 1700 | 52.25 | >90% | 0.75 |
|  |  | 39.36 | >90% | 2.0 |
|  |  | 29.66 | >90% | 5.0 |

While most catalysts show a decrease in conversion between 0.5 and 2 hours, some catalysts, such as catalyst 1, show an initial increase in activity, followed by a slow decrease after 2 hours TOS.

The data in Table 2 show that while most catalysts show a drop in conversion between 0.5 and 2 hours TOS, all, at 2 hours TOS, have a significantly higher activity than that of comparative catalyst 1 (insufficient pore volume), even at 0.5 hours TOS.

What is claimed is:

1. A process for preparing a reaction product comprising an alpha-methylene lactone of the Formula II, said process comprising reacting a lactone of the Formula I with formaldehyde

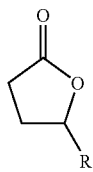

I

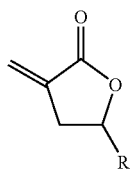

II wherein R is selected from the group consisting of hydrogen, methyl, ethyl, and straight or branched $C_3$–$C_5$ alkyl;

at a temperature in the range of from about 150° C. to about 450° C. in the presence of a catalyst;

said catalyst being made by a process comprising:
(a) contacting (i) porous silica, optionally containing a first element, said first element being one, two, or three members selected from the group consisting of aluminum, zirconium and titanium, said silica having a pore volume of at least 0.4 cc/g attributable to pores having a diameter between 65 and 3200 Angstroms, with (ii) a solution comprising a solvent and an organic compound of a second element, said second element being one, two, three, four or five members selected from the group consisting of sodium, potassium, rubidium, cesium, and barium;
(b) drying the product of step (a) to remove at least a portion of said solvent;
(c) heating the product of step (b) to a temperature in the range of 350° C. to 550° C. to produce a catalyst precursor,
(d) flushing at a preselected flow rate an oxygen-containing gas over said catalyst precursor either during step (c), or after step (c) while the temperature is still in the range of 350° C. to 550° C. to produce a catalyst candidate comprising the second element in an amount from about 0.1% to about 40% by weight of the combined weight of the catalyst candidate and the second element, or the combined weight of the catalyst candidate containing the first element and the second element;
(e) determining by porosimetry whether said catalyst candidate has a pore volume of at least about 0.3 cubic centimeters per gram of catalyst attributable to pores having a diameter between 65 and 3200 Angstroms; and
(f) if said catalyst candidate does not have a pore volume of at least about 0.3 cubic centimeters per gram of catalyst attributable to pores having a diameter between 65 and 3200 Angstroms, repeating, optionally more than once, steps (a) through (e) using in step (d) flow rates successively greater than said preselected flow rate until the catalyst candidate has a pore volume of at least about 0.3 cubic centimeters per gram of catalyst attributable to pores having a diameter between 65 and 3200 Angstroms.

2. The process of claim 1 wherein the porosimetry is mercury porosimetry.

3. The process of claim 1 wherein R is hydrogen or methyl.

4. The process of claim 1 further comprising separating said alpha methylene lactone from said reaction product.

5. A catalyst for preparing a reaction product comprising an alpha-methylene lactone of the Formula II, said process comprising reacting a lactone of the Formula I with formaldehyde

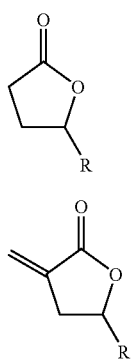

I

II wherein R is selected from the group consisting of hydrogen, methyl, ethyl, and straight or branched $C_3$–$C_5$ alkyl;

said catalyst made by a process comprising:
(a) contacting (i) porous silica, optionally containing at least one first element, said first element being one, two, or three members selected from the group consisting of aluminum, zirconium and titanium, said silica having a pore volume of at least 0.4 cc/g attributable to pores having a pore diameter between 65 and 3200 Angstroms, with (ii) a solution comprising a solvent and an organic compound of a second element, said second element being one, two, three, four or five members selected from the group consisting of sodium, potassium, rubidium, cesium, and barium;
(b) drying the product of step (a) to remove at least a portion of said solvent;
(c) heating the product of step (b) to a temperature in the range of 350° C. to 550° C. to produce a catalyst precursor;
(d) flushing at a preselected flow rate an oxygen-containing gas over said catalyst precursor either during step (a), or after step (a) while the temperature is still in the range of 350° C. to 550° C. to produce a catalyst candidate comprising the second element in an amount from about 0.1% to about 40% by weight of the combined weight of the catalyst candidate and the second element, or the combined weight of the catalyst candidate containing the first element and the second element;

(e) determining by porosimetry whether said catalyst candidate has a pore volume of at least about 0.3 cubic centimeters per gram of catalyst attributable to pores having a diameter between 65 and 3200 Angstroms; and (f) if said catalyst candidate does not have a pore volume of at least about 0.3 cubic centimeters per gram of catalyst attributable to pores having a diameter between 65 and 3200 Angstroms, repeating, optionally more than once, steps (a) through (e) using in step (d) flow rates successively greeter than said preselected flow rate until the catalyst candidate has a pore volume of at least about 0.3 cubic centimeters per gram of catalyst attributable to pores having a diameter between 65 and 3200 Angstroms.

6. The catalyst of claim 5 wherein the porosimetry is mercury porosimetry.

7. The catalyst of claim 5, wherein the organic compound in step (a) is an alkoxide having from 1 to 20 carbon atoms in the alkoxy group.

8. The catalyst of claim 5, wherein the second element is barium.

* * * * *